US009612232B2

(12) United States Patent
Montgomery et al.

(10) Patent No.: US 9,612,232 B2
(45) Date of Patent: Apr. 4, 2017

(54) STATIC GEL STRENGTH MEASUREMENT APPARATUS AND METHOD

(71) Applicants: Grafton Montgomery, Houston, TX (US); Guadalupe Hernandez Serafin, Houston, TX (US); David Hoffman, Houston, TX (US)

(72) Inventors: Grafton Montgomery, Houston, TX (US); Guadalupe Hernandez Serafin, Houston, TX (US); David Hoffman, Houston, TX (US)

(73) Assignee: OFI Testing Equipment, Inc., Houston, TX (US)

( * ) Notice: Subject to any disclaimer, the term of this patent is extended or adjusted under 35 U.S.C. 154(b) by 239 days.

(21) Appl. No.: 14/593,927

(22) Filed: Jan. 9, 2015

(65) Prior Publication Data

US 2015/0198512 A1    Jul. 16, 2015

Related U.S. Application Data

(60) Provisional application No. 61/926,274, filed on Jan. 11, 2014.

(51) Int. Cl.
*G01N 3/24* (2006.01)
*G01N 33/38* (2006.01)
*G01N 11/14* (2006.01)

(52) U.S. Cl.
CPC ........... *G01N 33/383* (2013.01); *G01N 11/14* (2013.01); *G01N 2203/0092* (2013.01)

(58) Field of Classification Search
USPC .................................................. 73/843, 841
See application file for complete search history.

(56) References Cited

U.S. PATENT DOCUMENTS

| 4,622,846 | A | * | 11/1986 | Moon, Jr. | G01N 11/14 73/54.28 |
| 5,315,864 | A | * | 5/1994 | Surjaatmadja | G01N 11/14 73/54.32 |
| 5,472,577 | A | * | 12/1995 | Porter | F04B 17/00 204/220 |
| 7,681,459 | B1 | * | 3/2010 | Yang | G01N 3/08 73/760 |

\* cited by examiner

*Primary Examiner* — Clayton E Laballe
*Assistant Examiner* — Warren K Fenwick
(74) *Attorney, Agent, or Firm* — Keeling Law, LLC; Kenneth A. Keeling; Mark S. Solomon

(57) ABSTRACT

A fluid properties measurement apparatus for use with a conventional high temperature high pressure test cell includes a load cell assembly and a drive motor that drives a rotating shaft magnetically connected to a vane assembly having multiple vane elements, wherein the motor rotates in response to reactive forces of a fluid sample and the load cell assembly measures reactive forces of the sample. In one embodiment, a stepper motor allows for precise shaft rotation. A method of measuring fluid properties includes frequent measurements throughout a complete rotation cycle of a vane assembly within a test cell. A system interference profile is generated which identifies stress variations resulting from various system components throughout the cycle. Measurements of a sample's fluid properties are likewise performed to obtain a profile. Comparison of the sample profile with the interference profile provides fluid properties measurement independent of stress variations resulting from various system components.

11 Claims, 6 Drawing Sheets

STATIC GEL STRENGTH MEASUREMENT APPARATUS AND METHOD

CROSS-REFERENCE TO RELATED APPLICATIONS

This application claims the benefit of U.S. Provisional Application No. 61/926,274 filed on Jan. 11, 2014, which application is incorporated herein by reference as if reproduced in full below.

STATEMENT REGARDING FEDERALLY SPONSORED RESEARCH OR DEVELOPMENT

Not applicable.

FIELD OF THE DISCLOSURE

This invention relates generally to testing equipment used to measure properties of materials and chemical systems, and more specifically to a method of measurement of cement static gel strength of a sample by incremental mapping of shear resistance force during full (360 degree) rotation of a paddle immersed in the sample.

BACKGROUND

In the oil and gas industry, it is imperative to know and understand the material properties of compositions used during drilling and exploration and to determine how these properties are affected by temperature, pressure, and time, including determination of cement mechanical and static strength variations as a function of time, temperature, and pressure.

Static gel strength is a measurement of shear strength (stress) and is derived from force required to initiate flow of a static fluid. Static gel strength may be measured in pascals (newtons per square meter) or in pounds per area unit.

Conventional gel strength measurement systems use a paddle in a test cell. The cement is placed in the test cell at determined pressure and temperature and allowed to begin curing. The paddle is rotated in relation to the test cell. Torsional stress is determined from forces on the test cell at various time intervals to determine gel strength at user defined time intervals.

Conventional systems for measuring gel strength include a Chandler Model 5265 SGSA apparatus (manufactured by Chandler Engineering, Inc., Broken Arrow, Okla.) for measurement of gel strength and compressive strength of a cement slurry, a Fann Instruments Model 101677665 MACS II Multiple Analysis Cement System (Manufactured by Fann Instrument Company, Houston, Tex.), and a CTE Model 15-400 RP Consistometer/Gel Strength apparatus (Manufactured by Cement Test Equipment, Inc., Tulsa Okla.). The Chandler apparatus measures gel strength using an acoustic transducer. The Fann Instruments system and the Cement Test Equipment apparatus measure gel strength with a torque transducer.

A conventional method of accounting for friction and other forces in the testing assembly is to determine an initial peak value of system force with a known sample, such as water, using such peak value as a base value, and assigning such value as the "zero value" of the system. This method may result in relatively large measurement errors of the sample as the system forces vary as the paddle or sample is rotated. The relative error may be particularly high when testing low viscosity samples. In addition, deduction of a zero value from sample measurements and consequent disregard for values below zero ignores potentially valuable sample measurements.

The paddle of conventional systems comprises two flat elements on opposing sides of a central rotating shaft, each flat element attached at one edge to the shaft. The two elements are aligned to extend in a common plane.

BRIEF SUMMARY OF THE DISCLOSURE

The present invention comprises a measuring system for use with a conventional high temperature high pressure (HPHT) test cell having an outer magnetic drive and motor driving a rotating inner magnetic shaft, a rotating vane assembly having multiple vane elements for rotation in the sample, the drive motor mounted on a motor mount, the motor mount and drive motor rotatable in relation to a base, a load cell assembly intermediate the motor mount assembly and the base, the motor mount and motor biased in response to reactive forces of the sample, the load cell determining reactive forces of the sample. An embodiment of the present invention uses a stepper motor allowing precise shaft rotation.

A method of the present invention provides relatively precise measurement of gel strength independent of variations resulting from varying friction forces within the test system. Gel strength of a sample is measured throughout a complete rotation of the paddle within the test cell with measurements during a preliminary stage utilizing a standard sample low viscosity fluid. Utilizing frequent measurements taken during a complete rotation cycle, an interference profile is identified, such interference profile identifying stress variations resulting from various system components throughout the cycle. A test sample, such as a cement sample, is then introduced into the test cell. Gel strength measurements of the sample are taken during a complete rotation cycle, resulting in identification of a gel strength profile. The gel strength profile is then compared with the interference profile to determine gel strength measurements independent of stress variations resulting from various system components. In an exemplary embodiment at least one interference profile is developed utilizing water as the standard sample. In an exemplary embodiment multiple gel strength measurements are determined, including profiles before and after an initial curing period, and further including profiles determined during an extended curing process.

BRIEF DESCRIPTION OF THE DRAWINGS

For a more complete understanding of the exemplary embodiments, reference is now made to the following Description of Embodiments of the Invention, taken in conjunction with the accompanying drawings, in which.

DESCRIPTION OF EXEMPLARY EMBODIMENTS OF THE INVENTION

Figure 1:
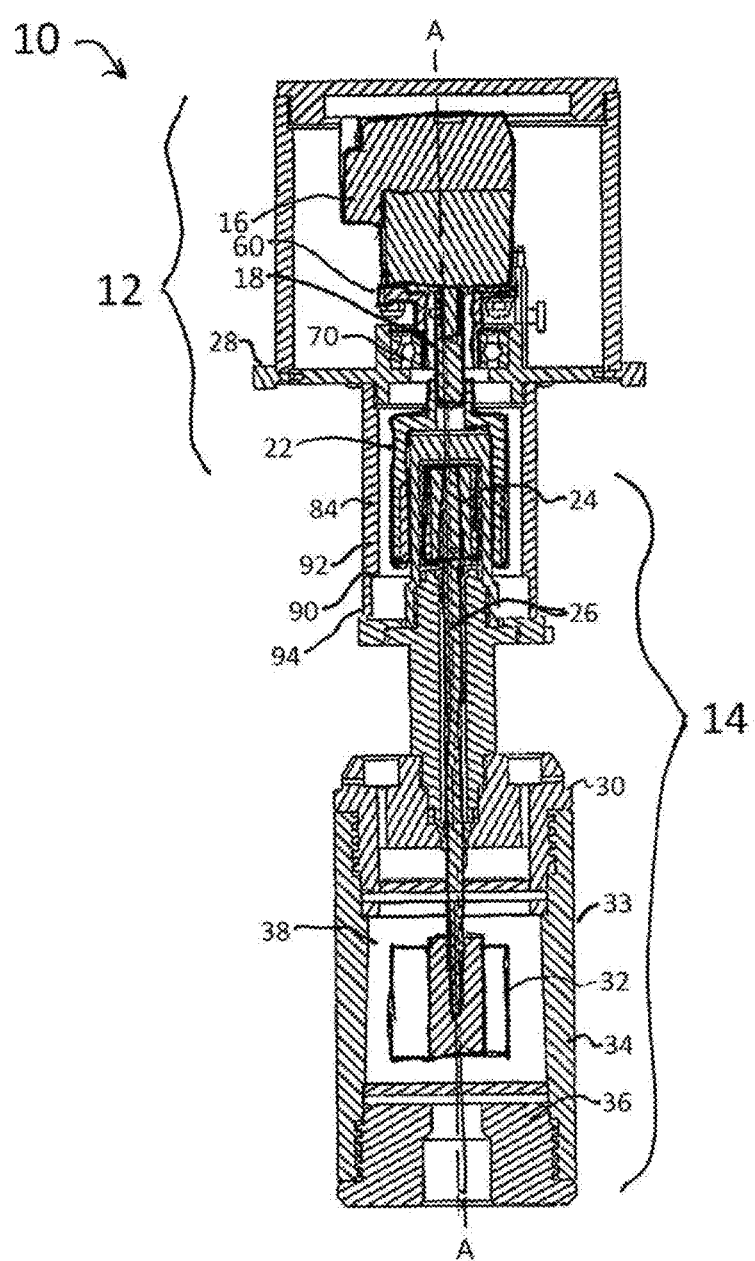
FIG. 1 depicts a section view representing components of a static gel strength measurement device of an embodiment of the present invention.

The exemplary embodiment is best understood by referring to the drawings, like numerals being used for like and corresponding parts of the various drawings.

The directions lower and upper as used in this specification are used for descriptive purposes only and it will be understood by one having skill in the art that different orientations are possible.

Referring to FIG. 1, a section view represents components of an embodiment of a static gel strength measurement apparatus 10. Static gel strength measuring apparatus 10 includes a drive assembly 12 and a cell assembly 14. Drive assembly 12 includes a motor 16 having a motor drive shaft 18. Motor 16 is supported on a motor mount/mounting base 60. Motor mount 60 is supported on drive base 28. Drive magnet assembly 22 is attached to the lower end of drive shaft 18. Motor 16 is operable to rotate drive shaft 18 which in turn rotates drive magnet assembly 22.

In an exemplary embodiment, motor 16 is a stepper motor. More specifically, motor 16 is a brushless direct current electric motor that provides rotation in incremental equal steps. Accordingly, angular rotation of drive shaft 18 may be commanded to rotate at any level of angular rotation without a feedback sensor. In like manner, motor 16 may be operated to hold or reverse movement of drive shaft 18 as determined. In an exemplary embodiment, stepper motor 16 provides for 50,000 steps of movement to achieve 360° rotation of drive shaft 18. In such embodiment, each step comprises 0.0072 angular degree of rotation.

Drive magnet assembly 22 is configured to drive a proximately and concentrically arranged driven magnet assembly 24 and driven shaft 26.

Figure 2:
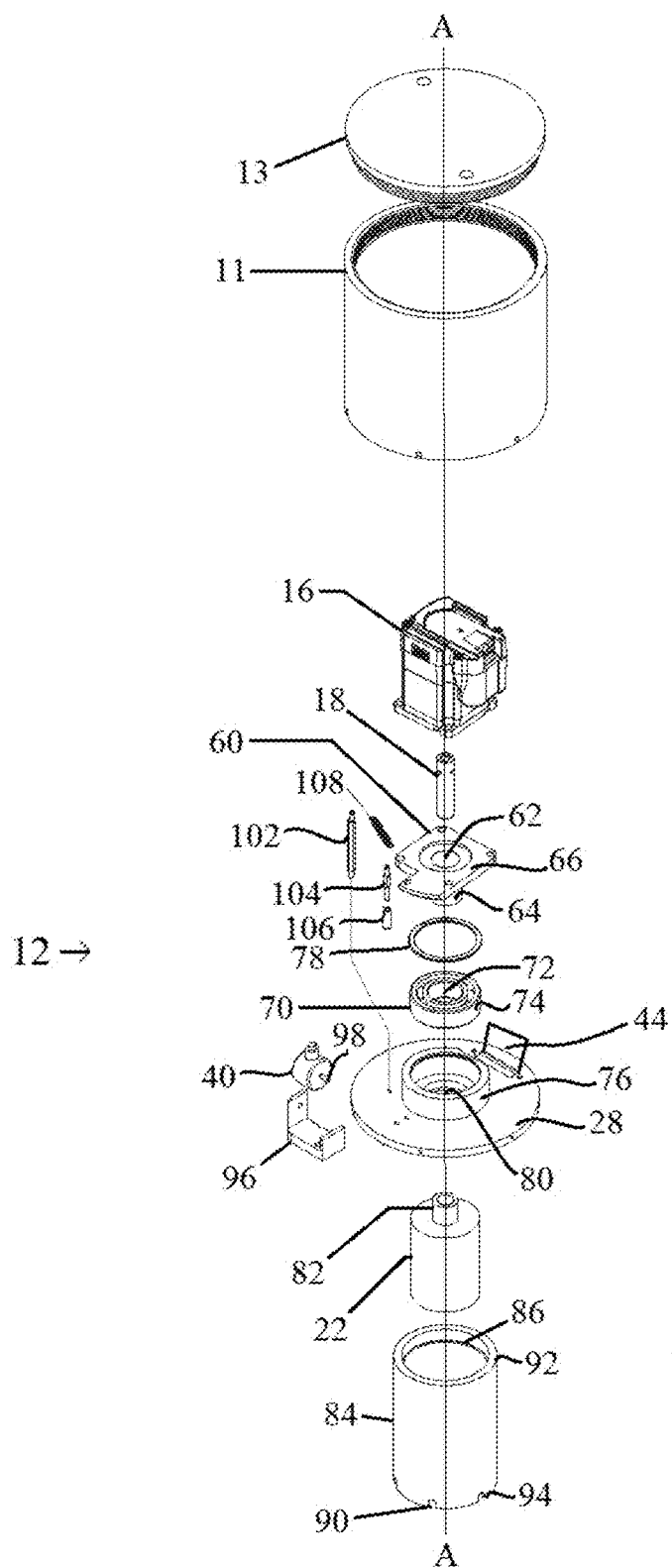
FIG. 2 depicts a drive assembly of an embodiment of the present invention.

Referring to FIG. 2 (which shows optional drive cover body 11 and optional drive cover cap 13), motor 16 is fixedly mounted on motor mount 60. Motor mount 60 includes a mount flange 66 and a collar 64. Collar 64 extends downwardly from mount flange 66. A central opening 62 is provided in motor mount 60. Drive shaft 18 extends through opening 62. Drive shaft 18 is rotatable in relation to base 28.

Collar 64 is connected to inner race 72 of bearing 70. Bearing 70 is a cylindrical bearing having inner race 72 and outer race 74. Outer race 74 of bearing 70 is held in a fixed lateral position by base connector 76. Base connector 76 in an upwardly-extending cylindrical element fixedly attached to base 28. Retaining ring 78 retains bearing 70 is a fixed vertical position in relation to base 28. An opening 80 is provided in the center of base 28. Drive shaft 18 extends through interior of inner race 72 of bearing 70 and through opening 80. Drive shaft 18 is connected to drive magnet assembly 22 at connector 82 at an upper end of drive magnet assembly 22.

Outer race 74 of bearing 70 is supported on base 28. Bearing 70 is constructed and arranged to allow rotation of inner race 72 in relation to outer race 74 and base 28. As motor mount 60 is supported on inner race 72 and motor 16 is fixedly attached to motor mount 60, motor 16 is displaceable in relation to base 28.

Drive assembly support 84 is connected to base 28 and extends downwardly therefrom. Drive assembly support 84 comprises a hollow cylinder defined by cylinder wall 92. In the embodiment depicted, upper end 86 of drive assembly support 84 is threaded. A downwardly extending cylindrical extension 88 (not shown in FIG. 2) of base 28 is provided with corresponding threading for attachment of drive assembly support 84 to base 28.

A countersunk shoulder 90 is provided proximate the lower end 94 of drive assembly support 84.

A force measurement device, such as but not limited to, a load cell, is employed in various embodiments of the present invention. In one embodiment, a load cell 40, which may comprise a strain gauge, piezoelectric, hydraulic, pneumatic, or any other suitable type of load cell, is mounted on load cell bracket 96. Load cell bracket 96 is fixedly attached to base 28. Load cell sensor 98 extends laterally from load cell 40. A base post 102 is mounted on base 28 extending upwardly therefrom. A mount post 104 is mounted on motor mount flange 66. A spring 108 is connected to each of base post 102 and mount post 104. Spring 108 biases base post 102 and mount post 104 to a base orientation with respect to each other. A contact post 106 extends downwardly from mount post 104. Contact post 106 is constructed and arranged to contact load cell sensor 98.

A processor 44 is positioned on drive base 28. Processor 44 is electronically connected to motor 16, to load cell 40, and to other processors including processors within computer 50 (not shown). Force readings determined by load cell 40 via sensor 98 are communicated to processor 44. Force readings determined by load cell 40 comprise determinations of force applied by rotational movement of motor 16 and motor mount 60 in relation to base 28, as detected by sensor 98. In an exemplary embodiment, rotated positions of stepper motor 16 are determined by a separate processor, not shown.

Figure 3:
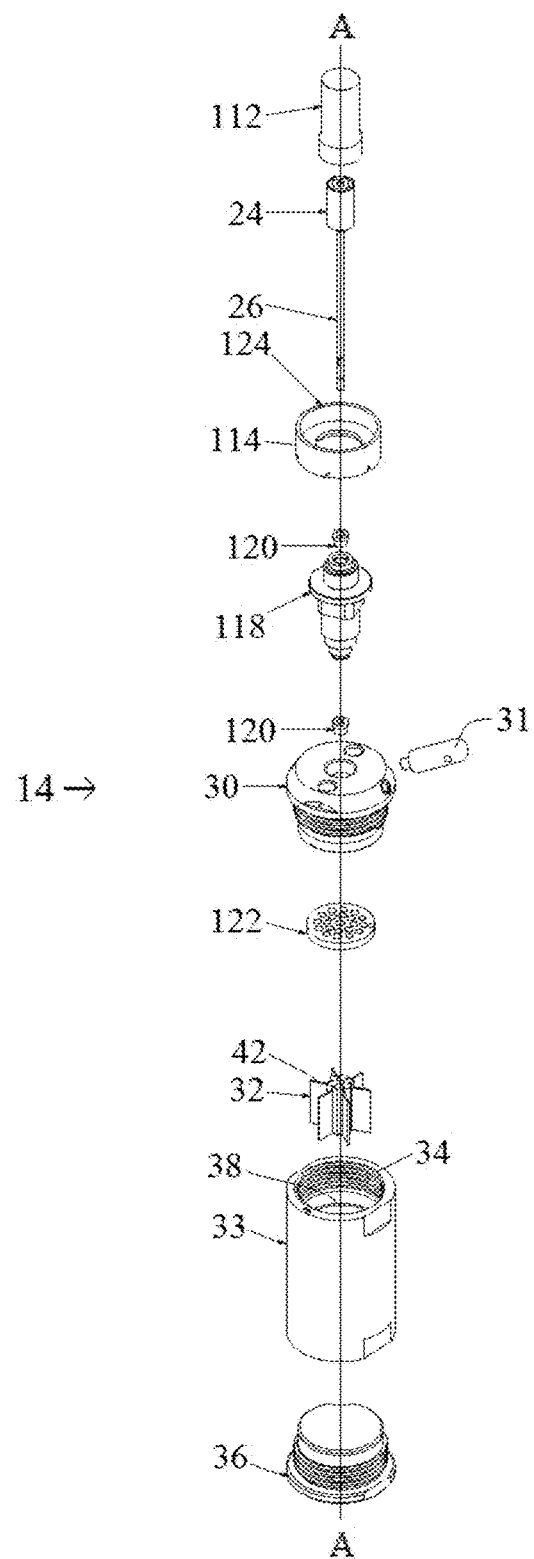
FIG. 3 depicts a cell assembly of an embodiment of the present invention.

Referring to FIG. 3 together with FIG. 1, cell assembly 14 includes a driven magnet assembly 24. Driven magnet assembly 24 is connected to an upper end of driven shaft 26. A driven magnet cover 112 is provided exterior of driven magnet assembly 24. Rotation of driven magnet assembly 24 results in rotation of driven shaft 26. Driven shaft 26 extends at its lower end into a sample chamber 38 of a test cell 33. Driven shaft 26 extends through upper plug 30 of test cell 33. Test cell 33 is a high temperature high pressure test cell having a generally cylindrical cell body 34, an upper plug 30 and a lower plug 36. Sample chamber 38 is interior of cell body 34, upper plug 30 and lower plug 36. Upper plug 30 may accommodate one or more handles 31.

In the exemplary embodiment, a vane assembly 32 is connected at the lower end of driven shaft 26. Vane assembly 32 is located within sample chamber 38 for engagement with a sample (not shown) to be positioned in sample chamber 38. Vane assembly 32 comprises a plurality of vane elements 42, each vane element 42 connected to driven shaft 26 at one side. In an exemplary embodiment, vane assembly 32 comprises six vane elements 42, the vane elements 42 arranged to extend at equal angular intervals from driven shaft 26. In alternative embodiments, vane assembly 32 comprises four elements 42.

In an alternative embodiment, a conventional paddle have two vane elements 42 may be utilized.

Cell assembly 14 further comprises base flange 114 supported on an adaptor assembly 118. Base flange 114 is sized and constructed to be slidably received within the lower end 94 of drive assembly support 84 with the upper end 124 of flange 114 abutting countersunk shoulder 90. Base flange 114 is connected to adaptor assembly 118. Bushings 120 are provided proximate the upper and lower ends of adaptor assembly 118.

A diaphragm 122 is provided in sample chamber 38 intermediate vane assembly 32 and upper plug 30.

All of base flange 114, adaptor 118, bushings 120, upper plug 30 and diaphragm 122 are provided with central openings to allow driven shaft 26 to extend through.

Upon attachment of cell assembly 14 to drive assembly 12, each of drive shaft 18, drive magnet assembly 22, driven magnet assembly 24, driven shaft 26, and vane 32 is concentrically aligned on central axis A-A. Drive assembly 12 is operable to rotate drive shaft 18 with consequent rotation of drive magnet assembly 22. Drive magnet assembly 22 concurrently rotates, via magnet coupling thereto, driven magnet assembly 24, and thereby driven shaft 26 and vane assembly 32.

Operation

In an embodiment of the present invention, a sample (not shown) is provided in sample chamber 38 and filled to a specified level such that vane assembly 32 will be submerged in the sample upon insertion. Assembled components, including driven magnet cover 112, driven magnet assembly 24, driven shaft 26, base flange 114, adaptor assembly 118, bushings 120, upper plug 30, diaphragm 122, and vane assembly 32, are connected to test cell 33 with upper plug 30 tightly affixed. A pressurization medium, such as water, is used to fill the remainder of the sample chamber 38.

Motor 16 of drive assembly 12 is operated at a determined speed and duration. Motor 16 rotates drive shaft 18 and drive magnet assembly 22. Drive magnet assembly 22 rotates driven magnet assembly 24, via magnetic coupling there between, and thereby driven shaft 26, causing vane assembly 32 to rotate within the sample.

Resistance of the sample to rotation of vane assembly 32 results in a reactive force, such force resulting from resistance of the sample to rotation of driven shaft 26 and drive shaft 18. Such reactive force angularly biases motor 16. As motor 16 is fixedly attached to motor mount 60, motor 16 and motor mount 60 both rotate in response to sample resistance. Rotation force of motor mount 60 is measured as a force measurement at load cell 40. As the lateral distance of load cell sensor 98 from axis A-A is known, the resistive force of the sample may be determined by torque calculations. Accordingly, load cell 40 pressure forces indicate resistance of the sample to rotating movement of vane assembly 32. Multiple determinations of resistance pressures may be made at predetermined time intervals to determine variations in resistive forces at determined time intervals. In application such multiple determinations indicate shear resistance of a sample at specific time intervals.

As stepper motor 16 is moveable in known increments, stepper motor 16 may be operated to rotate at known intervals. Operation of stepper motor 16 at known rotation speeds with concurrent sample shear resistance measurements provides basic data to determine gel strength of a sample.

During operation of apparatus 10, reactive force measurements at load cell sensor 98 are accumulated at determined time intervals. Rotational position of driven shaft 26, which is coincident with rotational position of drive shaft 18, is determined at determined time intervals. Accumulated data allows determination of changes in sample shear resistance to rotation of vane assembly 32. Accordingly, shear resistance of a sample may be determined at specified time intervals.

Method

As with any mechanical apparatus, apparatus 10 is subject to resistance forces other than simply resistance of a sample to shear. By way of example, other forces involving resistance include resistance of bearings and bushings. Apparatus 10 inherent resistance is referred to herein as system drag. Empirical determinations indicate system drag is not consistent during a full rotation of driven shaft 26.

Figure 4:
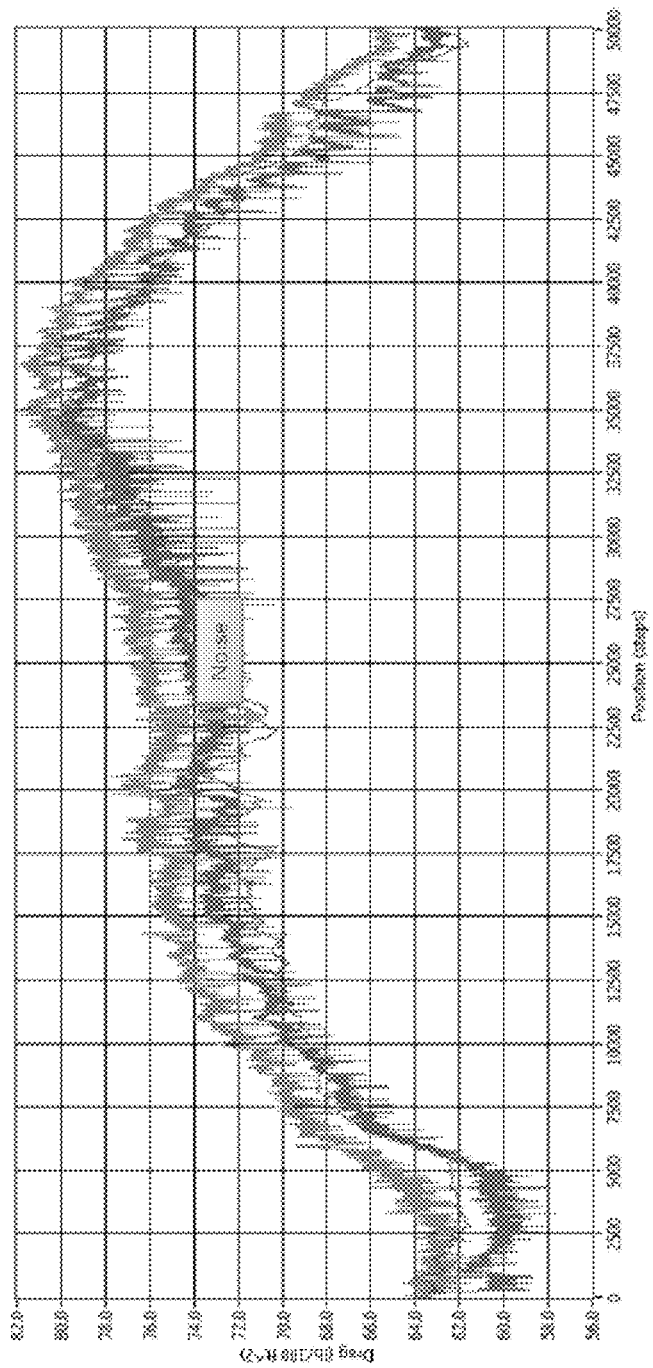
FIG. 4 depicts a zero data profile result in graphic form.
Figure 5:
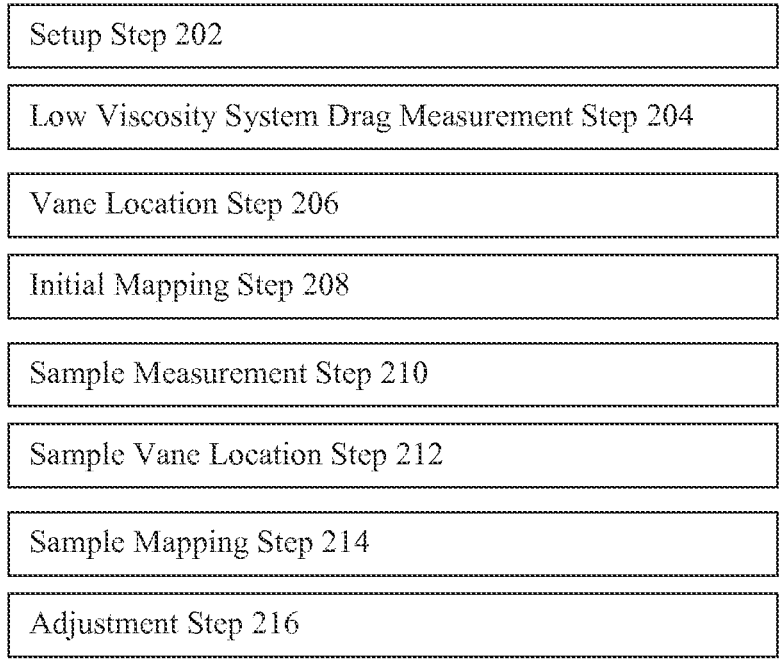
FIG. 5 depicts a method of an embodiment of the invention.
Figure 6:
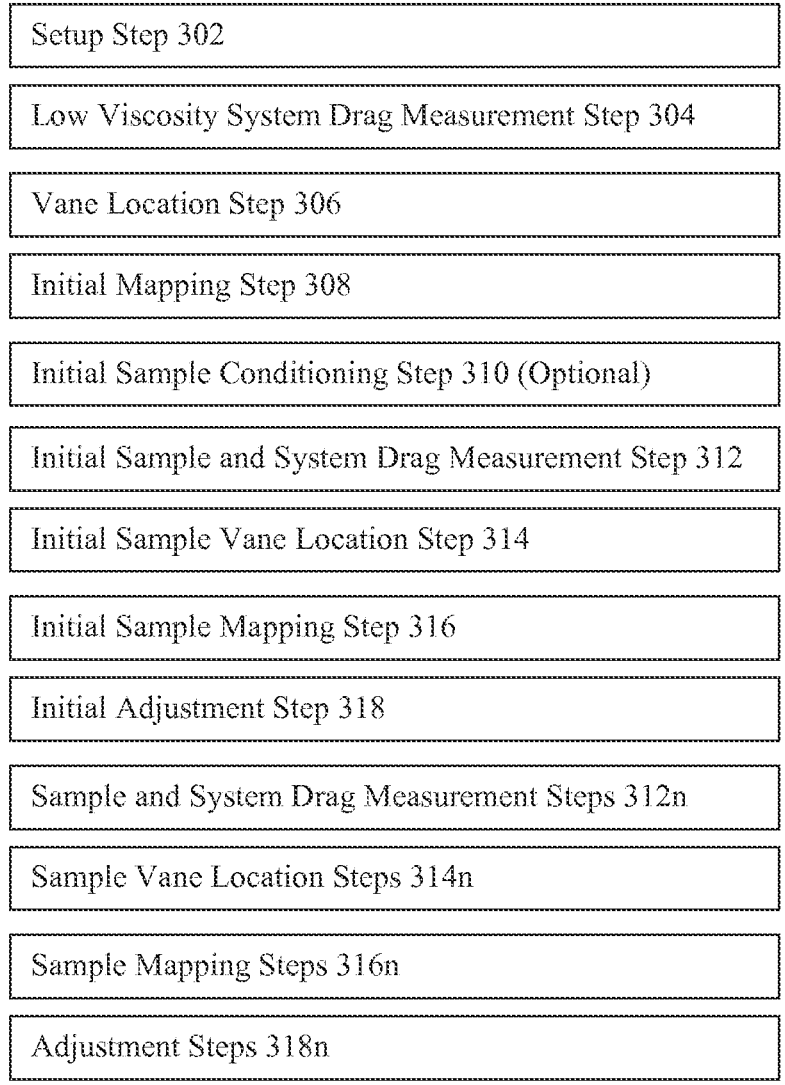
FIG. 6 depicts a method of an embodiment of the invention.

In an exemplary application of the operation described herein, apparatus 10 was operated in a test mode with a sample of water at 73° F. and atmospheric pressure. In such exemplary test, apparatus 10 was operated during full rotation cycle by stepper motor 16 at varying speeds. Specifically, motor 16 was operated at 1 revolution per minute, at 0.1 revolutions per minute and at 0.01 revolutions per minute. Resistance was determined by load cell sensor 98 at multiple driven shaft rotation locations. Resistance was determined to vary from 59 lbs./100 sq. ft. to 81 lbs./100 sq. ft. Resistance variation occurred in a pattern related to rotational position. Resistance patterns were consistent at all three revolution speeds. An exemplary output of resistance patterns is attached as FIG. 4. Referring to FIG. 4, a stepper motor was utilized providing 50,000 steps per revolution of driven shaft 26. Accordingly, FIG. 4 depicts measurements taken during a 360° revolution of driven shaft 26.

As used herein, mapping refers to organization of measurement data in relation to angular rotation positions of the vane assembly such that system drag variations resulting from angular rotation are correlated from one series of measurements to another series of measurements.

A method 200, an embodiment of a method of the present invention, comprises a method of determining shear resistance of a sample in a test cell with corrective adjustment for system drag involving the following steps.

A setup step 202 of providing a measurement apparatus of the type having a test cell, a vane assembly for rotating in a fluid placed in the test cell, a motor for rotating the vane assembly via magnetic coupling, and a sensor for determining fluid shear resistance.

A low viscosity system drag measurement step 204 of determining shear resistance and system drag of a known, low viscosity fluid in the test cell, said step comprising rotating the vane assembly in the low viscosity fluid for at least one full vane rotation and taking multiple shear resistance measurements during vane rotation.

A vane location step 206 of determining multiple angular rotation positions of the vane assembly during step 204 corresponding to respective shear resistance measurements.

An initial mapping step 208 of mapping fluid shear resistance and system drag in relation to vane location as utilized by step 204 and determined by step 206.

A sample measurement step 210 of determining shear resistance and system drag of a sample, said step comprising rotating the vane assembly in the sample for at least one full vane rotation and taking multiple shear resistance measurements during vane rotation.

A sample vane location step 212 of determining multiple angular rotation positions of the vane assembly during step 210 corresponding to respective shear resistance measurements.

A sample mapping step 214 of mapping shear resistance and system drag in relation to vane assembly location as utilized by step 210 and determined by step 212.

An adjustment step 216 comprising adjustment of sample measurements pursuant to steps 210, 212, and 214 in comparison with low viscosity fluid measurements pursuant to steps 204, 206, and 208 to account for system drag.

Method 200 provides a conceptual framework for adjustment of test sample shear resistance measurements. Actual application of the concepts outlined herein may require more nuanced calculations within the scope of the described method 200.

Multiple sample vane location steps 212, sample mapping steps 214, and adjustment steps 216 may be conducted over time to determine adjusted sample measurements as a function of time.

A method 300, an embodiment of a method of the present invention, comprises a method of determining shear resistance of a sample at determined time intervals with corrective adjustment for system drag involving the following steps.

A setup step 302 of providing a measurement apparatus of the type having a test cell, a vane assembly for rotating in a fluid in the test cell, a motor for rotating the vane assembly via magnetic coupling, and a sensor for determining fluid shear resistance.

A low viscosity system drag measurement step 304 of determining shear resistance and system drag of a known low viscosity fluid, said step comprising rotating the vane assembly in the low viscosity fluid for at least one full vane rotation and taking multiple shear resistance measurements during vane rotation.

A vane location step 306 of determining multiple angular rotation positions of the vane assembly during step 304 corresponding to respective shear resistance measurements.

An initial mapping step 308 of mapping shear resistance and system drag in relation to vane location as utilized by step 304 and determined by step 306.

An optional initial sample conditioning step 310 of allowing an initial cure time of a sample placed in the test cell.

An initial sample and system drag measurement step 312 of determining shear resistance and system drag of the sample placed in the cell, said step comprising rotating the vane assembly in the sample for at least one full vane rotation and taking multiple shear resistance measurements during vane rotation.

An initial sample vane location step 314 of determining multiple angular rotation positions of the vane assembly during step 312 corresponding to respective shear resistance measurements.

An initial sample mapping step 316 of mapping shear resistance and system drag in relation to vane location as utilized by step 312 and determined by step 314.

An initial adjustment step 318 comprising adjustment of specific sample force determinations of steps 312, 314, and 316 in comparison to respective corresponding measurements of steps 304, 306 and 308.

One or more sample measurement steps 312n, each of the n steps 312 comprising determining shear resistance and system drag of the sample place in the test cell, and each of the said n steps 312 comprising rotating the vane assembly in the sample for at least one full vane rotation and taking multiple shear resistance measurements during vane rotation.

One or more sample vane location steps 314n of determining multiple angular rotation positions of the vane assembly during each of the n steps 312 corresponding to respective shear resistance measurements.

One or more sample mapping steps 316n of mapping shear resistance and system drag in relation to vane location as utilized by the n steps 312 and determined by the n steps 314.

One or more adjustment steps 318n comprising adjustment of specific sample force determinations of n steps 312, n steps 314, and n steps 316, in comparison to respective corresponding measurements of step 304, step 306, and step 308. In each of steps 312n, 314n, 316n, and 318n, "n" represents an integer greater than or equal to one.

In an exemplary embodiment multiple subsequent sample measurement steps 312n, vane locations steps 314n, and mapping steps 316n are conducted during time periods with multiple adjustment steps 318n, the multiple iterations of said steps identifying changes, if any, in shear resistance of the sample over time.

The foregoing methods are more readily practiced by use of computer 50 and associated software. With particular reference to a cement mixture, initial zero sample measurement data is accumulated, multiple subsequent sample measurements are accumulated over time, and the subsequent sample measurements are adjusted to account for system drag. Depending on the cement mixture composition, pressure and temperature, the material may either start the gelation period and begin setting up (hardening) or remain in the fluid state as a function of time and temperature. Software may be provided to map the 360° torsional forces of the vane assembly on the load cell during the low viscosity sample measurement so system drag with a viscous sample is known. After conditioning and at the beginning of the cure process, the initial sample measurement test indicates initial shear resistance of the sample during intervals of a 360° rotation cycle of the shaft and vane assembly. Multiple subsequent sample measurement tests indicate shear resistance of the sample at 360° rotation intervals of the shaft and vane assembly. Gel strength measurements (reflecting setting up and hardening of the cement sample) are determined as differences between the original and/or early force values and subsequent force values with the advantages of differentiating force elements at various vane assembly angular positions to account for system drag.

Various embodiments will be understood from the foregoing description, and it will be apparent that, although embodiments have been described in detail, various changes, substitutions, and alterations may be made in the manner, procedure and/or details thereof without departing from the spirit and scope or sacrificing any of its material advantages, the forms hereinbefore described being merely exemplary embodiments thereof.

We claim:

1. An apparatus for measuring properties of a fluid comprising:
   a drive assembly and a cell assembly;
   the drive assembly comprising:
   a. a magnetic drive motor mounted on a motor mount,
   b. a base,
   c. a first rotating drive shaft rotatable, directly or indirectly, by the motor,
   d. a second rotating drive shaft rotatable, directly or indirectly, by the first rotating drive shaft, and
   e. a load cell;
   wherein:
   1. the motor and motor mount are rotatable in relation to the base,
   2. the drive shafts are rotatable in relation to the base,
   3. the load cell is disposed intermediate the motor mount and the base, and
   4. the second rotating drive shaft is connected to a vane assembly;
   the cell assembly comprising a high temperature high pressure test cell defining a cell chamber;
   wherein;
   1. the vane assembly is extendable into the cell chamber; and 2. the load cell is adapted to determine reactive motor rotation forces in relation to the base.

2. The apparatus of claim 1, wherein the motor comprises a stepper motor.

3. The apparatus of claim 2, wherein the stepper motor is adapted to provide 50,000 steps of movement to achieve 360 degree rotation of the drive shaft.

4. The apparatus of claim 1, wherein the vane assembly comprises vane elements that are disposed at equal angular intervals with respect to the second rotating drive shaft, and wherein the number of vane elements is 2, 3, 4, 5, or 6.

5. The apparatus of claim 1, wherein the cell chamber is adapted to accommodate a cement fluid.

6. A method of determining shear resistance of a fluid sample in a test cell comprising:
   A. a setup step comprising providing a measurement apparatus adapted to contain a sample in a test cell, a vane assembly for rotating in the sample fluid placed in the test cell, a magnetic stepper motor for rotating the vane assembly, and a sensor for determining fluid shear resistance of the sample fluid;
   B. a low viscosity system drag measurement step of determining shear resistance and system drag of a known low viscosity fluid in the test cell, comprising rotating the vane assembly in the low viscosity fluid for at least one full vane rotation and taking multiple shear resistance measurements during vane rotation;
   C. a vane location step of determining the multiple angular rotation positions the vane assembly occupied when the shear resistance measurements were taken during the low viscosity system drag measurement step;
   D. an initial mapping step of mapping fluid shear resistance and system drag measurements in relation to vane assembly locations utilized in the low viscosity system drag measurement step and determined in the vane location step;
   E. a sample measurement step of determining shear resistance and system drag of the fluid sample, comprising rotating the vane assembly in the fluid sample for at least one full vane rotation and taking multiple shear resistance measurements during vane rotation;
   F. a sample vane location step of determining the multiple angular rotation positions the vane assembly occupied when the shear resistance measurements were taken during the sample measurement step;
   G. a sample mapping step of mapping shear resistance and system drag in relation to vane assembly locations utilized in the sample measurement step and determined in the sample vane location step; and
   H. an adjustment step of adjusting sample shear resistance measurements, wherein the adjustment comprises comparison of the information obtained by performing the sample measurement step, the sample vane location step, and the sample mapping step, with the information obtained by performing the low viscosity system drag measurement step, the vane location step, and the initial mapping step.

7. The method of claim 6, wherein the fluid sample is a cement.

8. The method of claim 6, wherein one or more steps selected from the group consisting of:
   a. the sample vane location step;
   b. the sample mapping step; and
   c. the adjustment step;
are performed more than once.

9. A method of determining shear resistance of a fluid sample in a test cell at various time intervals comprising:
   A. a setup step comprising providing a measurement apparatus adapted to contain a sample in a test cell, a vane assembly for rotating in the fluid sample placed in the test cell, a magnetic stepper motor for rotating the vane assembly, and a sensor for determining fluid shear resistance of the sample fluid;
   B. a low viscosity system drag measurement step of determining shear resistance and system drag of a known low viscosity fluid in the test cell, comprising rotating the vane assembly in the low viscosity fluid for at least one full vane rotation and taking multiple shear resistance measurements during vane rotation;
   C. a vane location step of determining the multiple angular rotation positions the vane assembly occupied when the shear resistance measurements were taken during the low viscosity system drag measurement step;
   D. an initial mapping step of mapping fluid shear resistance and system drag measurements in relation to vane assembly locations utilized in the low viscosity system drag measurement step and determined in the vane location step;
   E. an initial sample measurement step of determining shear resistance and system drag of the fluid sample, comprising rotating the vane assembly in the fluid sample for at least one full vane rotation and taking multiple shear resistance measurements during vane rotation;
   F. an initial sample vane location step of determining the multiple angular rotation positions the vane assembly occupied when the shear resistance measurements were taken during the sample measurement step;
   G. an initial sample mapping step of mapping shear resistance and system drag in relation to vane assembly locations utilized in the sample measurement step and determined in the sample vane location step;
   H. an initial adjustment step of adjusting sample shear resistance measurements, wherein the adjustment comprises comparison of the information obtained by performing the initial sample measurement step, the initial sample vane location step, and the initial sample mapping step, with the information obtained by performing the low viscosity system drag measurement step, the vane location step, and the initial mapping step; and
   I. one or more additional steps selected from the group consisting of:
      1. one or more sample measurement steps of determining shear resistance and system drag of the fluid sample, comprising rotating the vane assembly in the fluid sample for at least one full vane rotation and taking multiple shear resistance measurements during vane rotation;
      2. one or more sample vane location steps of determining the multiple angular rotation positions the vane assembly occupied when the shear resistance measurements were taken during the corresponding one or more sample measurement steps; and
      3. one or more sample mapping steps of mapping shear resistance and system drag in relation to vane assembly locations utilized in the corresponding one or more sample measurement steps and determined in the corresponding one or more sample vane location steps.

10. The method of claim 9, wherein an initial sample conditioning step, comprising allowing an initial cure time of the sample in the test cell, is performed before the initial sample measurement step.

11. The method of claim 9, wherein the fluid sample is a cement.

* * * * *